(12) United States Patent
Uemura et al.

(10) Patent No.: US 6,635,770 B1
(45) Date of Patent: Oct. 21, 2003

(54) PROCESS FOR PRODUCING HEXAHYDROTHIENO (3,4-D)IMMIDAZOLE-2,4-DIONES

(75) Inventors: Toshitsugi Uemura, Toyonaka (JP); Mamoru Shirahata, Oita (JP); Yasunobu Miyamoto, Oita (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/544,472

(22) Filed: Apr. 7, 2000

(30) Foreign Application Priority Data

Apr. 8, 1999 (JP) .......................... 11-101235
Sep. 6, 1999 (JP) .......................... 11-251414

(51) Int. Cl.[7] .......................... C07D 495/04
(52) U.S. Cl. .......................... 548/303.7
(58) Field of Search .......................... 548/303.7

(56) References Cited

U.S. PATENT DOCUMENTS 5,969,149 A * 10/1999 Tani et al. ............ 548/303.7

FOREIGN PATENT DOCUMENTS

| JP | 4537776 | B  |   | 11/1970 |
|----|---------|----|---|---------|
| JP | 4742793 | A  |   | 12/1972 |
| JP | 5014692 | A  |   | 2/1975  |
| JP | 5024287 | A  |   | 3/1975  |
| JP | 5058088 | A  |   | 5/1975  |
| JP | 5327279 | B  |   | 8/1978  |
| JP | 54-112886 |  | * | 9/1979  |
| JP | 627196  | B2 |   | 2/1987  |
| JP | 8217779 | A  |   | 8/1996  |
| JP | 10-231298 |  | * | 9/1998  |

OTHER PUBLICATIONS

Shimaji et al., CA 92:41955, 1980.*
Hirata et al., CA 129:216619, 1998.*
An English translation of JP 54–112886, Sep. 1979.*
An English translation of JP 10–231298, Sep. 1998.*
Kogure et al., CA 78:97660m, Apr. 16, 1973.*
Katsura Kogure et al., Conversion of Anhydride to Thiolactone in Biotin Synthesis, Agr. Biol. Chem., 40(8), 1976, pp. 1657–1658.

von M. Gerecke, et al., Biotin Synthesis, Preparation of (3aS, 6aR)–1,3–Dibenzyltetrahydro–4H–Thieno [3,4–d] Imidazole–2,4(1H)–Dione, Helv. Chim. Acta, 1970, 53(5), pp. 991–999.

* cited by examiner

Primary Examiner—Laura L. Stockton
(74) Attorney, Agent, or Firm—Birch, Stewart, Kolasch & Birch, LLP

(57) ABSTRACT

There is disclosed a process for producing hexahydrothieno [3,4-d]imidazole-2,4-diones of formula (1):

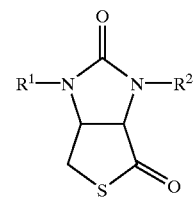

(1)

wherein $R^1$ and $R^2$ are the same or different and independently represent a hydrogen atom, a lower alkyl, alkenyl, aryl or aralkyl group all of which may be substituted, which is characterized by reacting hexahydrofuro[3,4-d]imidazole-2,4-diones of formula (2):

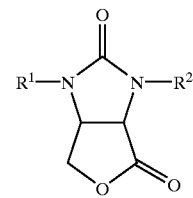

(2)

wherein $R^1$ and $R^2$ are the same as defined above, with thioamide in the presence of alkali hydrogen sulfide, sulfur and a basic compound selected from alkali metal carbonate, alkali metal sulfide, an alkali metal salt of the carboxylic acid having C2–C6 carbon atoms and an organic base having C6–C10 carbon atoms.

19 Claims, No Drawings

PROCESS FOR PRODUCING HEXAHYDROTHIENO (3,4-D)IMMIDAZOLE-2,4-DIONES

BACKGROUND OF THE INVENTION

1. Field of the Invention

The present invention relates to a process for producing hexahydrothieno[3,4-d]imidazole-2,4-diones. More particularly, the present invention concerns a process for producing hexahydrothieno[3,4-d]imidazole-2,4-diones which are useful as an intermediate for the preparation of biotin (vitamin H).

2. Description of Related Art

Heretofore, as a method for producing hexahydrothieno[3,4-d]imidazole-2,4-diones using hexahydrofuro[3,4-d]imidazole-2,4-diones as a raw material, the following methods have been known.

1. A method in which hexahydrofuro[3,4-d]imidazole-2,4-dione is reacted with an alkali metal salt of thioacetic acid as disclosed in Helvetica Chimica Acta, 53, 991–999 (1970), and 2. a method in which hexahydrofuro[3,4-d]imidazole-2,4-dione is reacted with thioamides as disclosed in Japanese examined patent publication Shou 62-7196.

However, the first method required stoichiometric amount of unstable and expensive alkali metal salt of thioacetic acid, and the second method is not always satisfactory in yield.

SUMMARY OF THE INVENTION

An object of the present invention is to provide an industrially advantageous process for producing hexahydrothieno[3,4-d]imidazole-2,4-diones of the following formula (1).

The present inventors have intensively studied to solve the above problem. As a result, they have found an industrially advantageous process for producing hexahydrothieno[3,4-d]imidazole-2,4-diones which are important as the intermediate of biotin, and they have accomplished the present invention.

The present invention provides:

1. A process for producing hexahydrothieno[3,4-d]imidazole-2,4-diones of formula (1):

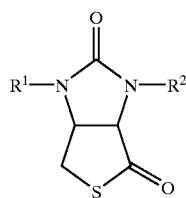

wherein $R^1$ and $R^2$ are the same or different and independently represent a hydrogen atom, an alkyl, alkenyl, aryl or aralkyl group all of which may be substituted, which comprises: reacting hexahydrofuro[3,4-d]imidazole-2,4-diones of formula (2):

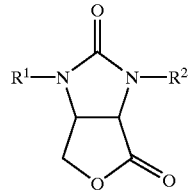

wherein $R^1$ and $R^2$ are the same as defined above with thioamide in the presence of alkali hydrogen sulfide, sulfur and a basic compound selected from alkali metal carbonate, alkali metal sulfide, an alkali metal salt of the carboxylic acid having C2–C6 carbon atoms and an organic base having C6–C10 carbon atoms.

DESCRIPTION OF THE PREFERRED EMBODIMENTS

First, a description will be made to a process for producing hexahydrothieno[3,4-d]imidazole-2,4-diones of the formula (1) as defined above, which comprises: reacting hexahydrofuro[3,4-d]imidazole-2,4-diones of formula (2) as defined above with thioamide in the presence of alkali hydrogen sulfide, sulfur and a basic compound selected from alkali metal carbonate, alkali metal sulfide, an alkali metal salt of the carboxylic acid having (C2–C6) carbon atoms and an organic base having C6–C10 carbon atoms.

The compound of formula (2) may be an optical isomer, a mixture thereof, or a racemate, which can be optionally selected.

In hexahydrofuro[3,4-d]imidazole-2,4-diones of formula (2) and hexahydrothieno[3,4-d]imidazole-2,4-diones of formula (1), $R^1$ and $R^2$ are the same or different and independently represent a hydrogen atom, an alkyl, alkenyl, aryl or aralkyl group all of which may be substituted. Compounds of formula (2) wherein $R^1$ and $R^2$ are the same are preferably used.

Examples of the alkyl group which may be substituted include, for example, a straight or branched chain (C1–C8) alkyl group such as a methyl group, an ethyl group, n-propyl group, an i-propyl group, an n-butyl group, a t-butyl group, an n-hexyl group, and an n-octyl group and the alkyl group may be substituted with at least one group selected from a halogen atom (e.g., a fluorine atom, a chlorine atom, a bromine atom, and an iodine atom), an (C1–C3) alkoxy group (e.g., a methoxy group, an ethoxy group, and an i-propxy group). Specific examples of the alkyl group include a haloalkyl group such as a fluoromethyl group, chloromethyl group or a chloroethyl group, and an alkoxyalkyl such as a methoxymethyl group. Among these groups, (C1–C4) alkyl groups are preferably used.

Examples of the alkenyl group which may be substituted include a straight or branched chain (C2–C8) alkenyl group such as a vinyl group, an allyl group, 2-butenyl group or a 3-methyl-2-butenyl group. Said alkenyl group may be substituted with at least one group selected from a halogen atom and an alkoxy group as described above for the alkyl group. Specific examples thereof include a haloalkenyl group and an alkoxyalkenyl group.

Among the alkenyl groups, preferred are (C3–C4)alkenyl groups.

The aryl and aralkyl group may be substituted on the aryl groups with at least one group selected from an (C1–C3)

alkyl group, an (C1–C3)alkoxy group, a nitro group and a halogen atom (e.g., fluorine, chlorine, bromine, iodine).

Examples of the aryl group which may be substituted include a phenyl group, a naphthyl group, a chlorophenyl group, a methoxyphenyl group, a nitrophenyl group a xylyl group, a tolyl group and 1-methylnaphthyl group and 2-methylnaphthyl group. The phenyl, tolyl and naphthyl groups are preferred.

Examples of the aralkyl group which may be substituted include an aryl-substituted (C1–C3)alkyl group such as a benzyl group, a phenylethyl group, a naphthylmethyl group, a methoxybenzyl group, a bromobenzyl group, a nitrobenzyl group, and a methylbenzyl group.

Among them, the benzyl group, methoxybenzyl group are preferred and particularly the benzyl group is preferred.

Specific examples of the compound of formula (2) include:

hexahydrofuro[3,4-d]imidazole-2,4-dione,
1,3-dimethylhxahydrofuro[3,4-d]imidazole-2,4-dione,
1,3-diethylhexahydrofuro[3,4-d]imidazole-2,4-dione,
1,3-di(n-propyl)hexahydrofuro[3,4-d]imidazole-2,4-dione,
1,3-diallylhexahydrofuro[3,4-d]imidazole-2,4-dione,
1,3-di(2-butenyl)hexahydrofuro[3,4-d]imidazole-2,4-dione,
1,3-di(2-methyl-3-butenyl)hexahydrofuro[3,4-d]imidazole-2,4-dione,
1,3-diphenylhexahydrofuro[3,4-d]imidazole-2,4-dione,
1,3-ditolylhexahydrofuro[3,4-d]imidazole-2,4-dione,
1,3-diphenylhexahydrofuro[3,4-d]imidazole-2,4-dione,
1,3-di(methoxybenzyl)hexahydrofuro[3,4-d]imidazole-2,4-dione and
1,3-di(bromobenzyl)hexahydrofuro[3,4-d]imidazole-2,4-dione.

1,3-diallylhexahydrofuro[3,4-d]imidazole-2,4-dione, 1,3-dibenzylhexahydrofuro[3,4-d]imidazole-2,4-dione and 1,3-di(methoxybenzyl)hexahydrofuro[3,4-d]imidazole-2,4-dione are preferred.

Examples of the thioamide to be reacted with the compound of formula (2) include, for example, a (C2–C4) aliphatic thioamide such as thioacetamide or thiopropionamide, a C6 aromatic thioamide which may be substituted with at least one group selected from a halogen atom, a nitro group, an amino group, a hydroxy group, and a (C1–C3) alkoxy group. Specific examples thereof include thiobenzamide, thiochlorobenzamide, thiobromobenzamide, thionitrobenzamide, thioaminobenzamide, thiomethoxybenzamide and thiohydroxybenzamide.

Preferred is the aliphatic thioamide, and thioacetamide is preferably used because of its good availability.

Examples of the alkali hydrogen sulfide include, for example, an alkali metal hydrogen sulfide such as sodium hydrogen sulfide or potassium hydrogen sulfide, and an alkaline earth metal hydrogen sulfide such as calcium hydrogen sulfide. Preferred is the alkali metal hydrogen sulfide, particularly preferred is sodium hydrogen sulfide. Said alkali hydrogen sulfide may be either anhydrous or hydrated. Said hydrated compound is usually used and the shape of the compound is not particularly limited.

Any types of sulfur (e.g. powder or lump) may be used. Preferred is powder sulfur.

The amount of the thioamide is usually 0.01 mole or more, preferably 0.05 mole or more, more preferably 0.1 mole or more per mole of the compound of formula (2).

The amount of the alkali hydrogen sulfide is usually 0.1 mole or more per mole of the compound of formula (2).

The amount of sulfur is usually 0.1 mole or more per mole of the compound of formula (2).

The total amount of thioamide, alkali hydrogen sulfide and sulfur to be used is usually 0.9 mole or more, preferably 1 mole or more, more preferably 1.2 moles or more per mole of the compound of formula (2), and said total amount is usually 2 moles or less, preferably 1.9 moles or less, more preferably 1.5 moles or less per mole of the compound of formula (2). The amount of thioamide, alkali hydrogen sulfide or sulfur may be optionally set within the above-described total amount range.

Examples of the basic compound to be used in the above reaction include
alkali metal carbonate (e.g., sodium carbonate, potassium carbonate),
alkali metal sulfide such as sodium sulfide,
an alkali metal salt of the carboxylic acid (e.g., aliphatic or aromatic carboxylic acid) having 2 to 6 carbon atoms such as an alkali metal salt of acetic acid, propionic acid, isobutyric acid or benzoic acid, and
an organic base having 6 to 10 carbon atoms (e.g., a (C6–C10) secondary or tertiary organic amine compound) such as triethylamine, triethanolamine, diisopropylamine, diisobutylamine, piperidine, pyrrolidine and N,N,N',N'-tetramethylethylenediamine, and a basic solvent as described below.

Among them, sodium acetate and potassium acetate are particularly preferred.

The amount of the basic compound is usually about 0.01–10 moles, preferably about 0.2–2 moles per mole of the compound of formula (2).

The reaction of the compound of formula (2) and thioamide is usually conducted in the presence of a solvent.

Examples of the solvent used in the reaction include:
an aprotic polar amide solvent such as N,N-dimethylformamide, N,N-dimethylacetamide, 1,3-dimethyl-2-imidazolidinone, tetramethylurea, hexamethylphosphoric triamide, N-methyl-2-pyrrolidone;
an aprotic polar solvent such as dimethyl sulfoxide and sulfolane;
a glycol including polyethylene glycol and a monoether and diether thereof such as ethylene glycol, 2-methoxyethanol, dimethoxyethane, diethylene glycol, diethylene glycol monomethyl ether, diethylene glycol dimethyl ether, triethylene glycol monomethyl ether, triethylene glycol dimethyl ether, and propyleneglycol;
a basic solvent such as N-methylmorpholine, diisopropylamine, triisopropylamine, tri-n-butylamine, β-picoline, γ-picoline, 2-methyl-5-ethylpyridine, quinoline, isoquinoline, N,N-dimethylaniline, N,N-diethylaniline, diazabicyclo[5,4,0]undec-7-ene; and a mixed solvent thereof.

Particularly, glycols are preferred, more preferred is polyethylene glycol. These solvent may be used by mixing with a solvent having lower polarity such as toluene, xylene and ethylbenzene.

Although the amount of the solvent is not particularly limited, it normally is about 10 parts by weight, preferably 5 parts by weight per 1 part by weight of the compound of formula (2).

Hexahydrofuro[3,4-d]imidazole-2,4-diones is usually reacted within a range of about 50–150° C., preferably within a range of about 70–120° C., more preferably 80–110° C., and the reaction may be conducted either under normal pressure, reduced pressure or pressure.

After completion of the reaction the reaction solution may be subjected to a conventional post-treatment such as concentration and or recrystallization by cooling to obtain the compound of formula (1), alternatively, the reaction solution may be acidified by contacting with an acid to obtain the desired product.

Said acidification of the reaction solution is usually conducted at a pH of usually 3 or less, preferably, 1 or less by contacting the reaction solution with an acidic aqueous solution (e.g. hydrochloric acid or sulfuric acid) or acetic acid usually at 0 to 100° C., preferably 10 to 70° C.

The product compound of formula (1) may be obtained either by cooling the acidified solution or extraction with a hydrophobic organic solvent where water may be added together with the organic solvent prior to acidification or later to facilitate a phase separation, and successively separated oil phase may be cooled to crystallize the product or concentrated.

Examples of the solvent to be used is aromatic hydrocarbon solvent such as toluene or xylene, and an ether solvent such as diethyl ether, an aliphatic hydrocarbon solvent such as hexane. The amount of said solvent is not particularly limited. The extraction is usually conducted at 0 to 100° C., preferably 10 to 70° C. Said acidification may be conducted in the presence of a metal such as tin, zinc, iron powder or the like to improve the reaction yield and obtain the desired compound with a good quality. The desired product of formula (1) may be obtained by the above-described post-treatment after removing solid material such as undissolved metal, if necessary. The metal is preferably used in a powder form.

The amount of the metal is normally about 5 moles or less, preferably about 3 moles or less per mol of the compound of formula (2) from economical view point.

Thus obtained product compound of formula (1) can be further purified by recrystallizing from
an ether solvent such as diethyl ether or methyl t-butyl ether,
a hydrocarbon solvent such as hexane or toluene,
alcohol solvent such as methanol, ethanol or 2-propanol, or
a mixed solvent of said alcohol solvent and water.

Specific examples of the compound of formula (1) include:

hexahydrothieno[3,4-d]imidazole-2,4-dione,
1,3-dimethylhexahydrofuro[3,4-d]imidazole-2,4-dione,
1,3-diethylhexahydrothieno[3,4-d]imidazole-2,4-dione,
1,3-di(n-propyl)hexahydrothieno[3,4-d]imidazole-2,4-dione,
1,3-diallylhexahydrothieno[3,4-d]imidazole-2,4-dione,
1,3-di(2-butenyl)hexahydrothieno[3,4-d]imidazole-2,4-dione,
1,3-di(2-methyl-3-butenyl)hexahydrothieno[3,4-d]imidazole-2,4-dione,
1,3-diphenylhexahydrothieno[3,4-d]imidazole-2,4-dione,
1,3-ditolylhexahydrothieno[3,4-d]imidazole-2,4-dione,
1,3-dibenzylhexahydrothieno[3,4-d]imidazole-2,4-dione,
1,3-di(methoxybenzyl)hexahydrothieno[3,4-d]imidazole-2,4-dione and
1,3-di(bromobenzyl)hexahydrothieno[3,4-d]imidazole-2,4-dione.

According to the process of the present invention, hexahydrothieno[3,4-d]imidazole-2,4-diones, which is useful as the intermediate for the preparation of biotin, can be produced industrially advantageously in a satisfactory yield by using inexpensive raw materials.

The following Examples further illustrate the present invention in detail, but are not to be construed to limit the scope of the invention thereto.

EXAMPLE 1

8.00 g of sodium hydrogen sulfide (hydrate: purity 70%) was added to a solution containing 59.40 g of 1,3-dibenzylhexahydrofuro[3,4-d]imidazole-2,4-dione, 3.75 g of thioacetamide, 9.28 g of sodium acetate, 3.84 g of sulfur and 87.64 g of polyethylene glycol (Average molecular weight: 600), and the resulting solution was heated up to 103° C. and stirred at the same temperature for 11 hours. Then the solution was cooled to 80° C., and 346.73 g of toluene and 185.53 g of water were added thereto. 16.05 g of zinc was added to the resulting mixture at 15° C. to 30° C. and 84.30 g of 35% hydrochloric acid was dropwise added. After the mixture was stirred for 12 hours at 45° C., water phase was separated. Obtained oil layer was washed with water and evaporated to give crude 1,3-dibenzylhexahydrothieno[3,4-d]imidazole-2,4-dione, which was recrystallized from a mixed solution of 2-propanol and water to give 55.89 g of crystals of 1,3-dibenzylhexahydrothieno[3,4-d]imidazole-2,4-dione. (Yield: 90% Purity:99.6%) Analysis of the filtrate obtained in the recrystallization process with liquid chromatography showed that yield in the reaction was 91%.

EXAMPLE 2

The reaction as described in Example 1 was conducted with the exception that the reaction temperature was set at 105° C. in place of 103° C. and reaction time at that temperature was 10 hours to give 55.61 g of crystal of cis-1,3-dibenzylhexahydrothieno[3,4-d]imidazole-2,4-dione in a yield of 89%. (Yield in the reaction was 90%)

EXAMPLE 3

15.99 g of sodium hydrogen sulfide (hydrate: purity 70%) was added to a solution containing 118.80 g of 1,3-dibenzylhexahydrofuro[3,4-d]imidazole-2,4-dione, 18.56 g of thioacetamide, 7.50 g of sodium acetate, 7.50 g of sulfur and 175.28 g of polyethylene glycol (Average molecular weight: 600), and the resulting solution was heated up to 105° C. and stirred at the same temperature for 10 hours. Then the solution was cooled to 80° C., and 693.77 g of toluene and 372.03 g of water were added thereto. 32.10 g of zinc was added to the resulting mixture at 15° C. to 30° C. and 168.61 g of 35% hydrochloric acid was dropwise added. After the mixture was stirred for 5 hours at 45° C. and for 3 hours at 60° C., water phase was separated. Obtained oil layer was washed with water and evaporated to give crude 1,3-dibenzylhexahydrothieno[3,4-d]imidazole-2,4-dione, which was recrystallized from a mixed solution of 2-propanol and water to give 111.08 g of crystals of 1,3-dibenzylhexahydrothieno[3,4-d]imidazole-2,4-dione. (Yield: 90%) Analysis of the filtrate obtained in the recrystallization process with liquid chromatography showed that yield in the reaction was 92%.

EXAMPLE 4

8.00 g of sodium hydrogen sulfide (hydrate: purity 70%) was added to a solution containing 59.43 g of 1,3-dibenzylhexahydrofuro[3,4-d]imidazole-2,4-dione, 1.88 g of thioacetamide, 9.28 g of sodium acetate, 4.50 g of sulfur and 87.68 g of polyethylene glycol (Average molecular weight: 600), and the resulting solution was heated up to 101° C. and stirred at the same temperature for 14 hours. Then the solution was cooled to 80° C., and 347.49 g of toluene and 185.81 g of water were added thereto. 17.35 g of zinc was added to the resulting mixture at 15° C. to 30°

C. and 84.92 g of 35% hydrochloric acid was dropwise added. After the mixture was stirred for 5 hours at 45° C. and at 60° C. for 3 hours, water phase was separated. Obtained oil layer was washed with water and evaporated to give crude 1,3-dibenzylhexahydrothieno[3,4-d]imidazole-2,4-dione, which was recrystallized from a mixed solution of 2-propanol and water to give 55.14 g of crystals of 1,3-dibenzylhexahydrothieno[3,4-d]imidazole-2,4-dione. (Yield: 88%) Analysis of the filtrate obtained in the recrystallization process with liquid chromatography showed that yield in the reaction was 90%.

EXAMPLE 5

8.00 g of sodium hydrogen sulfide (hydrate: purity 70%) was added to a solution containing 59.46 g of 1,3-dibenzylhexahydrofuro[3,4-d]imidazole-2,4-dione, 7.49 g of thioacetamide, 9.27 g of sodium acetate, 4.50 g of sulfur and 87.64 g of polyethylene glycol (Average molecular weight: 600), and the resulting solution was heated up to 101° C. and stirred at the same temperature for 8 hours. Then the solution was cooled to 80° C., and 346.85 g of toluene and 185.61 g of water were added thereto. 28.91 g of zinc was added to the resulting mixture at 15° C. to 30° C. and 141.28 g of 35% hydrochloric acid was dropwise added. After the mixture was stirred for 5 hours at 45° C. and at 60° C. for 3 hours, water phase was separated. Obtained oil layer was washed with water and evaporated to give crude 1,3-dibenzylhexahydrothieno[3,4-d]imidazole-2,4-dione, which was recrystallized from a mixed solution of 2-propanol and water to give 54.97 g of crystals of 1,3-dibenzylhexahydrothieno[3,4-d]imidazole-2,4-dione. (Yield: 84%) Analysis of the filtrate obtained in the recrystallization process with liquid chromatography showed that yield in the reaction was 86%.

EXAMPLE 6

The reaction as described in Example 4 was conducted with the exception that the reaction temperature was set at 109° C. in place of 101° C. and reaction time at that temperature was 12 hours to give 53.74 g of crystal of cis-1,3-dibenzylhexahydrothieno[3,4-d]imidazole-2,4-dione in a yield of 83%. (Yield in the reaction was 85%)

EXAMPLE 7

2.06 g of sodium hydrogen sulfide (hydrate: purity 70%) was added to a solution containing 59.40 g of 1,3-dibenzylhexahydrofuro[3,4-d]imidazole-2,4-dione, 15.00 g of thioacetamide, 9.28 g of sodium acetate, 3.00 g of sulfur and 87.60 g of polyethylene glycol (Average molecular weight: 600), and the resulting solution was heated up to 109° C. and stirred at the same temperature for 10 hours. Then the solution was cooled to 80° C., and 346.80 g of toluene and 185.6 g of water were added thereto. 15.00 g of zinc was added to the resulting mixture at 15° C. to 30° C. and 73.30 g of 35% hydrochloric acid was dropwise added. After the mixture was stirred for 5 hours at 45° C. and at 60° C. for 3 hours, water phase was separated. Obtained oil layer was washed with water and evaporated to give crude 1,3-dibenzylhexahydrothieno[3,4-d]imidazole-2,4-dione, which was recrystallized from a mixed solution of 2-propanol and water to give 52.81 g of crystals of 1,3-dibenzylhexahydrothieno[3,4-d]imidazole-2,4-dione. (Yield: 86%) Analysis of the filtrate obtained in the recrystallization process with liquid chromatography showed that yield in the reaction was 86%.

EXAMPLE 8

The reaction as described in Example 7 was conducted with the exception that the reaction time at 109° C. was 6 hours and 7.43 g of sodium hydrogen sulfide was used in place of 2.06 g of the same to give 54.37 g of crystal of cis-1,3-dibenzylhexahydrothieno[3,4-d]imidazole-2,4-dione in a yield of 84%.

What is claimed is:

1. A process for producing a hexahydrothieno[3,4-d] imidazole-2,4-dione of formula (1):

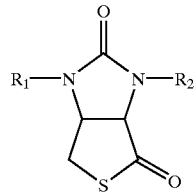

(1)

wherein $R^1$ and $R^2$ are the same or different and independently represent a hydrogen atom, a lower alkyl group, an alkenyl group, an aryl group or an aralkyl group all of which may be substituted, which comprises:

reacting a hexahydrofuro[3,4-d]imidazole-2,4-dione of formula (2):

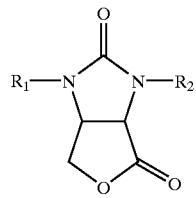

(2)

wherein $R^1$ and $R^2$ are the same as defined above with a thioamide in the presence of an alkali hydrogen sulfide, sulfur and a basic compound selected from an alkali metal carbonate, an alkali metal salt of the carboxylic acid having C2–C6 carbon atoms and an organic base having C6–C10 carbon atoms, wherein the total amount of thioamide, alkali hydrogen sulfide and sulfur is 1.5 moles or less per mol of the compound of formula (2).

2. A process according to claim 1, said alkali hydrogen sulfide is alkali metal hydrogen sulfide.

3. A process according to claim 2, wherein said alkali metal hydrogen sulfide is sodium hydrogen sulfide.

4. A process according to claim 1, which further comprises the step of: contacting the resulting reaction solution with an acid.

5. A process according to claim 4, wherein said reaction of the resulting reaction solution with an acid is conducted in the presence of a metal.

6. A process according to claim 5, wherein said metal is zinc, iron or tin.

7. The process according to claim 1, wherein the total amount of thioamide, alkali hydrogen sulfide and sulfur is 1 mol to 1.5 moles per mol of the compound of formula (2).

8. The process of claim 1, wherein the amount of thioamide is 0.01 mole or more per mole of the compound of formula 2.

9. The process of claim 1, wherein the amount of thioamide is 0.05 mole or more per mole of the compound of formula 2.

10. The process of claim 1, wherein the amount of thioamide is 0.1 mole or more per mole of the compound of formula 2.

11. The process of claim 1, wherein the amount of alkali hydrogen sulfide is 0.1 mole or more per mole of the compound of formula 2.

12. The process of claim 1, wherein the amount of sulfur is at least 0.1 mole per mole of the compound of formula 2.

13. The process of claim 1, wherein the amount of basic compound is 0.01 to 10 moles per mole of the compound of formula 2.

14. The process of claim 1, wherein the amount of basic compound is 0.02 to 2 moles per mole of the compound of formula 2.

15. The process of claim 1, wherein said alkali hydrogen sulfide is anhydrous.

16. The process of claim 1, wherein said alkali hydrogen sulfide is hydrated.

17. A process for producing a compound of formula (1):

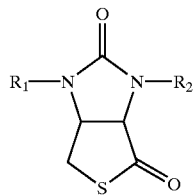

(1)

wherein $R^1$ and $R^2$ are the same or different and independently represent a hydrogen atom, a lower alkyl group, an alkenyl group, an aryl group or an aralkyl group, all of which may be substituted, said method comprising:

reacting a compound of formula (2):

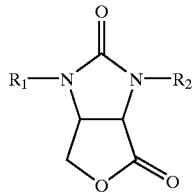

(2)

with a thioamide in the presence of
(A) an alkali hydrogen sulfide,
(B) sulfur, and
(C) a basic compound selected from the group consisting of
(1) an alkali metal carbonate,
(2) an alkali metal salt of the carboxylic acid having C2–C6 carbon atoms, and
(3) an organic base having C6–C10 carbon atoms,
wherein the amount of thioamide is 0.1 mole or more per mole of the compound of formula 2;
wherein the amount of alkali hydrogen sulfide is 0.1 mole or more per mole of the compound of formula 2;
wherein the amount of sulfur is at least 0.1 mole per mole of the compound of formula 2;
wherein the amount of basic compound is 0.02 to 2 moles per mole of the compound of formula 2; and
wherein the total amount of thioamide, alkali hydrogen sulfide and sulfur is 0.9 to 2.0 moles per mol of the compound of formula (2).

18. The method of claim 15, wherein total amount of thioamide, alkali hydrogen sulfide and sulfur is 1.0 to 1.5 moles per mol of the compound of formula (2).

19. The method of claim 15, wherein said thioamide is thioacetamide or thiopropionamide.

* * * * *